US012037312B2

(12) United States Patent
Hasenstab-Riedel et al.

(10) Patent No.: US 12,037,312 B2
(45) Date of Patent: Jul. 16, 2024

(54) PROCESS FOR THE PREPARATION OF FLUORINATED PEROXIDES

(71) Applicant: SOLVAY SA, Brussels (BE)

(72) Inventors: Sebastian Hasenstab-Riedel, Kleinmachnow (DE); Jan Hendrick Nissen, Berlin (DE); Helmut Beckers, Görlitz (DE); Simon Steinhauer, Berlin (DE); Thomas Drews, Berlin (DE); Holger Pernice, Schwanewede (DE)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 17/050,139

(22) PCT Filed: Apr. 25, 2019

(86) PCT No.: PCT/EP2019/060554
§ 371 (c)(1),
(2) Date: Oct. 23, 2020

(87) PCT Pub. No.: WO2019/207020
PCT Pub. Date: Oct. 31, 2019

(65) Prior Publication Data
US 2021/0094911 A1 Apr. 1, 2021

(30) Foreign Application Priority Data
Apr. 25, 2018 (EP) .................... 18169194

(51) Int. Cl.
*C07C 407/00* (2006.01)
*B01J 27/12* (2006.01)
*B01J 37/26* (2006.01)

(52) U.S. Cl.
CPC ............ *C07C 407/00* (2013.01); *B01J 27/12* (2013.01); *B01J 37/26* (2013.01)

(58) Field of Classification Search
None
See application file for complete search history.

(56) References Cited

U.S. PATENT DOCUMENTS

| 4,075,073 A | * | 2/1978 | Toy ............... C07C 407/00 204/157.9 |
| 10,283,234 B2 | | 5/2019 | Eicher et al. |
| 2007/0049774 A1 | | 3/2007 | Syvret et al. |
| 2018/0108451 A1 | | 4/2018 | Janssen et al. |

FOREIGN PATENT DOCUMENTS

| EP | 3078657 A1 | 10/2016 | |
| EP | 3309147 A1 | 4/2018 | |
| WO | WO-2016162572 A1 * | 10/2016 | ........... C07C 409/16 |

OTHER PUBLICATIONS

Schack, C. J. et al. "Chloroxyperfluoroalkanes" J. Am. Chem. Soc., (1969) 91, 2902 (Year: 1969).*
Gonzalez, A. C. et al. "The Kinetics and the Mechanism of the Thermal Reaction between Sulfurtetrafluoride (SF4) and Trifluoromethylhypofluorite (CF3OF) Chloroxyperfluoroalkanes" J. Am. Chem. Soc., (1969) 91, 2902 (Year: 1969).*

* cited by examiner

*Primary Examiner* — Medhanit W Bahta
(74) *Attorney, Agent, or Firm* — Osha Bergman Watanabe & Burton LLP

(57) ABSTRACT

The present invention relates to the preparation of perfluorinated or partially fluorinated peroxides which avoids the use of carbonyl fluoride ($COF_2$).

12 Claims, No Drawings

PROCESS FOR THE PREPARATION OF FLUORINATED PEROXIDES

This application is a U.S. national stage entry under 35 U.S.C. § 371 of International Application No. PCT/EP2019/060554 filed Apr. 25, 2019, which claims priority to European application No. EP 18169194.0, filed on Apr. 25, 2018. The entire contents of these applications are explicitly incorporated herein by this reference.

TECHNICAL FIELD

The present invention relates to the preparation of perfluorinated or partially fluorinated peroxides which avoids the use of carbonyl fluoride ($COF_2$).

BACKGROUND ART

Fluorinated peroxides are known. For example $CF_3$—O—O—$CF_3$ has been described in WO 2014/096414 as alternative to $SF_6$ and $N_2$ as dielectric insulating gas and its production has been described in US-A-2007/0049774. The European patent applications EP 3 078 657 and EP 3 309 147 both disclose certain fluorinated peroxide compounds and processes for their preparation. For instance, these documents disclose the reaction between the appropriate carbonyl fluoride and molecular fluorine, the reaction between the appropriate carbonyl fluoride, $COF_2$ and molecular fluorine, and the reaction between the appropriate carbonyl fluoride, oxyfluoride and molecular fluorine. However, the method of production described therein uses carbonyl fluoride ($COF_2$ and/or other appropriate carbonyl fluorides) as a reagent. Carbonyl fluoride is described to be extremely poisonous with a threshold limit value of 2 ppm for short-term exposure, it reacts violently with water and it is expensive. Besides, U.S. Pat. No. 4,075,073 discloses a method for synthesizing bis(perfluoro-t-butyl)peroxide through the photolysis of perfluoro-t-butyl hypofluorite in the presence of tetrafluorohydrazine $N_2F_4$. Tetrafluorohydrazine is a fluorine atom scavenger, which is difficult to prepare, highly hazardous and known to explode in the presence of organic material.

Thus, there is still a need for improved methods of production of perfluorinated and partially fluorinated peroxides.

DESCRIPTION OF THE INVENTION

The object of the present invention is to provide improved processes for the preparation of perfluorinated or partially fluorinated peroxides. This object and other objects are achieved by this invention. The processes of the present invention are advantageous in terms of improved yield, improved purity, improved selectivity, improved safety profile, improved cost of goods and/or improved energy consumption.

Accordingly a first aspect of the present invention concerns a process for the manufacture of a compound of formula $R^1R^2R^3C$—O—O—$CR^4R^5R^6$ wherein $R^1$ to $R^6$ are chosen independently from F or a perfluorinated or partially fluorinated linear or branched alkyl group comprising a step reacting a hypofluorite $R^1R^2R^3COF$ or a mixture of $R^1R^2R^3COF$ and $R^4R^5R^6COF$ and/or a hypochlorite $R^1R^2R^3COCl$ or a mixture of $R^1R^2R^3COCl$ and $R^4R^5R^6COCl$ in the absence of $COF_2$.

The term "in the absence of" should be understood that no $COF_2$ is added to the reaction mixture in order for the reaction to proceed. It should however not exclude traces of $COF_2$ being present, e.g. as impurity from an earlier reaction or as a side product formed in the inventive process.

According to one embodiment, the process according to the invention is carried out in the absence of $COF_2$ and $F_2$.

According to another embodiment, the process according to the invention is carried out in the absence of any carbonyl fluoride, in particular in the absence any carbonyl fluorides of formula R'R"R'"CC(O)F, wherein R', R" and R'" are selected independently from F or a perfluorinated or partially fluorinated linear or branched alkyl group. According to another embodiment, the process according to the invention is carried out in the absence of any highly hazardous compound, in particular in the absence of chlorine trifluoride $ClF_3$.

According to another embodiment, the process according to the invention is carried out in the absence of any fluorine atom scavenger, in particular in the absence of tetrafluorohydrazine $N_2F_4$.

The compound of formula $R^1R^2R^3C$—O—O—$CR^4R^5R^6$ can be a symmetric peroxide, i.e. the groups $R^1R^2R^3C$ and $CR^4R^5R^6$ are identical. In that case, the hypofluorite and/or hypochlorite used for the inventive process are the same, i.e. only one type of hypofluorite and/or hypochlorite is used in the reaction. The process to prepare such symmetrical peroxides is preferred.

The compound of formula $R^1R^2R^3C$—O—O—$CR^4R^5R^6$ can also be unsymmetrical, i.e. the groups $R^1R^2R^3C$ and $CR^4R^5R^6$ are different. In that case, a mixture of two different hypofluorites and/or hypochlorites is used for the inventive process.

Preferably, $R^1$ to $R^6$ are independently selected from the group consisting of F, $CF_3$, $C_2F_5$ and $C_3F_8$. Specifically the compound to be prepared is chosen from the group consisting of $(CF_3)_3C$—O—O—$CF_3$, $(C_2F_5)(CF_3)_2C$—O—O—$CF_3$, $(C_2F_5)_2(CF_3)C$—O—O—$CF_3$, $(C_2F_5)_3C$—O—O—$CF_3$, $(CF_3)_3C$—O—O—$C(CF_3)_3$, $(C_2F_5)(CF_3)_2C$—O—O—$C(CF_3)_3$, $(C_2F_5)_2(CF_3)C$—O—O—$C(CF_3)_3$, $(C_2F_5)_3C$—O—O—$C(CF_3)_3$, $(C_2F_5)(CF_3)_2C$—O—O—$C(C_2F_5)(CF_3)_2$, $(C_2F_5)_2(CF_3)C$—O—O—$C(C_2F_5)(CF_3)_2$, $(C_2F_5)_3C$—O—O—$C(C_2F_5)(CF_3)_2$, $(C_2F_5)_2(CF_3)C$—O—O—$C(C_2F_5)_2(CF_3)$, $(C_2F_5)_3C$—O—O—$C(C_2F_5)_2(CF_3)$, $(C_2F_5)_3C$—O—O—$C(C_2F_5)_3$, $(i-C_3F_7)(CF_3)_2C$—O—O—$CF_3$, $(i-C_3F_7)_2(CF_3)C$—O—O—$CF_3$, $(i-C_3F_7)_3C$—O—O—$CF_3$, $(i-C_3F_7)(CF_3)_2C$—O—O—$C(CF_3)_3$, $(i-C_3F_7)_2(CF_3)C$—O—O—$C(CF_3)_3$, $(i-C_3F_7)_3C$—O—O—$C(CF_3)_3$, $(i-C_3F_7)(CF_3)_2C$—O—O—$C(i-C_3F_7)(CF_3)_2$, $(i-C_3F_7)_2(CF_3)C$—O—O—$C(i-C_3F_7)(CF_3)_2$, $(i-C_3P_7)_3C$—O—O—$C(i-C_3F_7)(CF_3)_2$, $(i-C_3F_7)_2(CF_3)C$—O—O—$C(i-C_3F_7)_2(CF_3)$, $(i-C_3F_7)_3C$—O—O—$C(i-C_3F_7)_2(CF_3)$, $(i-C_3F_7)_3C$—O—O—$C(i-C_3F_7)_3$, $(i-C_3F_7)(CF_3)(C_2F_5)C$—O—O—$CF_3$, $(i-C_3F_7)(CF_3)(C_2F_5)C$—O—O—$C(CF_3)_3$, $(i-C_3F_7)(CF_3)(C_2F_5)C$—O—O—$C(i-C_3F_7)(CF_3)_2$, $(i-C_3F_7)(CF_3)(C_2F_5)C$—O—O—$C(i-C_3F_7)(C_2F_5)(CF_3)$, $(i-C_3F_7)(CF_3)(C_2F_5)C$—O—O—$C(i-C_3F_7)_2(CF_3)$, $(i-C_3F_7)(CF_3)(C_2F_5)C$—O—O—$C(i-C_3F_7)_3$ and $CF(CF_3)_2$—O—O—$CF(CF_3)_2$, $CF_3CF_2$—O—O—$CF_3CF_2$, $CF_3$—O—O—$CF_3CF_2$, $CF_3$—O—O—$CF_3$.

Also preferably, the hypofluorite $R^1R^2R^3COF$ and/or $R^4R^5R^6COF$ and/or the hypochlorite $R^1R^2R^3COCl$ and/or $R^4R^5R^6COCl$ are reacted with an inorganic fluoride or an inorganic chloride, more preferably with an inorganic fluoride selected from the group consisting of AgF, $AgF_2$, CuF, $CuF_2$, $BaF_2$, CsF, $NiF_2$, more preferably with a mixture of AgF and $AgF_2$.

According to a preferred embodiment, the mixture of AgF and $AgF_2$ is prepared by treating silver wool with elemental fluorine. The step of preparing the mixture of AgF/AgF$_2$ may preferably be conducted in a stainless steel container. According to a preferred embodiment, gaseous fluorine may be added to the silver wool in small portions up, while the pressure is preferably monitored to a value of about 2 bar. Addition of fluorine may be stopped when the consumption rate of fluorine had dropped to a few mbar per hour. This procedure may be started at ambient temperature, and the temperature may be increased up to 150° C. The preparation of the silver fluoride catalyst may take several days. We may assume that the preparation step is completed when approximately 95 mol-% of the fluorine was consumed.

Without wishing to be bound by any theory, the inventors believe that the silver fluoride material obtained by the process as disclosed above successfully convert the hypofluoride compounds into the corresponding peroxide according to the present invention, in the absence of COF$_2$, whereas commercially silver fluoride is less effective.

According to one preferred embodiment, one object of the present invention consists in a process for the manufacture of a compound of formula $R^1R^2R^3C$—O—O—$CR^4R^5R^6$, consisting in a first step consisting in preparing a mixture of AgF/AgF$_2$ by treating silver wool with elemental fluorine, and then a second step consisting in reacting a hypofluorite $R^1R^2R^3COF$ or a mixture of $R^1R^2R^3COF$ and $R^4R^5R^6COF$ and/or a hypochlorite $R^1R^2R^3COCl$ or a mixture of $R^1R^2R^3COCl$ and $R^4R^5R^6COCl$ with said mixture of AgF/AgF$_2$ in the absence of COF$_2$ ($R^1$, $R^2$, $R^3$, $R^4$, $R^5$ and $R^6$ having the meanings disclosed hereinabove).

The inorganic fluoride used in this preferred embodiment is more preferably used in at least stoichiometric amounts, i.e. it is not present only in catalytic amounts. Unlike a catalyst, the inorganic fluoride or chloride is undergoing a permanent chemical change in the reaction and preferably, is recovered and regenerated in a separate step. Preferably, the molar ratio of inorganic fluoride to hypofluorite $R^1R^2R^3COF$ and/or $R^4R^5R^6COF$ and/or the hypochlorite $R^1R^2R^3COCl$ and/or $R^4R^5R^6COCl$ is higher than 0.5, more preferably, higher than 0.6, 0.7, 0.8 or 0.9, most preferably higher than 1.0. Advantageously, it can also be used in excess with a molar ratio of higher than 1.5 and even 2.5.

Also preferably, the hypofluorite $R^1R^2R^3COF$ and/or $R^4R^5R^6COF$ and/or the hypochlorite $R^1R^2R^3COCl$ and/or $R^4R^5R^6COCl$ is reacted in a photochemical reaction, more preferably, the photochemical reaction is performed under irradiation with UV light of 200-400 nm wavelengths, most preferably between 200-300 nm.

The term "photochemical reaction" shall denote a chemical reaction caused by absorption of light, preferably UV light.

One other object of the present invention is a process for the manufacture of a compound of formula $R^1R^2R^3C$—O—O—$CR^4R^5R^6$ wherein $R^1$ to $R^6$ are independently chosen from the group consisting of F or a perfluorinated or partially fluorinated linear or branched alkyl group comprising a step reacting a hypochlorite $R^1R^2R^3COCl$ or a mixture of $R^1R^2R^3COCl$ and $R^4R^5R^6COCl$ in a photochemical reaction.

The hypochlorites $R^1R^2R^3COCl$ and/or $R^4R^5R^6COCl$ can be commercially obtained or, preferably, they may be prepared in a reaction of an alcohol $R^1R^2R^3COH$ and/or $R^4R^5R^6COH$ or ketones $R^1R^2C(O)$ and/or $R^3R^4C(O)$, wherein $R^1$ to $R^6$ are chosen independently from the group consisting of F or a perfluorinated or partially fluorinated linear or branched alkyl group, with an inorganic fluoride selected from the group consisting of AgF, AgF$_2$, CuF, CuF$_2$, BaF$_2$, CsF, NiF$_2$, preferably with CsF, and subsequently in a reaction in the presence of chlorine monofluoride (ClF). Thus, the alcohol $R^1R^2R^3COH$ and/or $R^4R^5R^6COH$ or ketones $R^1R^2C(O)$ and/or $R^3R^4C(O)$ are/is reacted in a first step with the inorganic fluoride, preferably with CsF, to form the corresponding $R^1R^2R^3COCs$ and/or $R^4R^5R^6COCs$, which is subsequently reacted with ClF to form the corresponding hypochlorites.

In another aspect, the invention concerns a process for the manufacture of a compound of formula $R^1R^2R^3C$—O—O—$CR^4R^5R^6$ wherein $R^1$ to $R^6$ are chosen independently from the group consisting of F or a perfluorinated or partially fluorinated linear or branched alkyl group comprising a step reacting a hypofluorite $R^1R^2R^3COF$ and/or $R^4R^5R^6COF$ with AgF, AgF$_2$, or a mixture of AgF and AgF$_2$. Preferably, the AgF, AgF$_2$, or the mixture of AgF and AgF$_2$ is used in a molar ratio of higher than 1.0 compared to the hypofluorite $R^1R^2R^3COF$ and/or $R^4R^5R^6COF$.

In the context of the present invention, the term "comprising" is intended to include the meaning of "consisting of". In the present disclosure, designations in singular are intended to include the plural. The expression "comprised between . . . and . . . " should be understood as including the limits.

In the present disclosure "alkyl" refers to a linear or branched saturated hydrocarbon, having preferably from 1 to 5 carbon atoms. Preferred examples of alkyl groups are methyl, ethyl, propyl, isopropyl, butyl, isobutyl and tert-butyl.

The term "perfluorinated alkyl" refers to a linear or branched saturated hydrocarbon, having preferably from 1 to 5 carbon atoms wherein all the hydrogen atoms have been replaced by fluorine. Preferred examples are $CF_3$, $CF_3CF_2$, $CF_3CF_2CF_2$, $(CF_3)_2CF$, $CF_3CF_2CF_2CF_2$, $CF_3CF_2(CF_3)CF_2$, $(CF_3)_3C$.

The term "partially fluorinated alkyl refers to a linear or branched saturated hydrocarbon, having preferably from 1 to 5 carbon atoms wherein at least one hydrogen atoms has been replaced by fluorine. Preferred examples are $CH_2F$, $CHF_2$, $CF_3CH_2$, $CF_3CHF$, $CF_3CH_2CH_2$, $CF_3CF_2CH_2$, $(CF_3)_2 CH$.

The compounds prepared according to the present invention can be used as electrolyte component in an electrochemical device, and more particularly in electronic displays or in energy storing and releasing devices. The compounds may be used as electrolyte component in one of the following electrochemical devices:

Electrochromic device: car or house windows, visors, eyeglasses,

Electrochromic flat screens: televisions, tablets, smartphones, connected devices, Secondary lithium batteries, lithium-sulfur batteries, lithium-air batteries, sodium batteries, High voltage batteries, Supercapacitors, in particular double-layer supercapacitors using an electrolyte, Energy generator, such as solar panels or organic type (OPV).

Preferably the electrochemical device may be a lithium-ion battery, a lithium-sulfur battery or a supercapacitor.

The compounds prepared according to the present invention may also be used as replacement for $SF_6$ as dielectric insulation gas.

Should the disclosure of any patents, patent applications and publications, which are incorporated herein by reference, conflicts with the description of the present invention to the extent that it may render a term unclear, the present description shall take precedence.

The invention will now be further described in examples, which are given by way of illustration and which are no intended to limit the specification or the claims in any manner.

EXAMPLE

Example 1

Preparation of the Silver Fluoride (AgF/AgF2) Catalyst

Silver wool (~20 g) was treated with elemental fluorine in a stainless steel container. The gaseous fluorine was added in small portions up to a pressure of 2 bar via a stainless steel gas-distribution line and a gas inlet-valve of the stainless steel container to the silver wool, while the pressure in the stainless steel line was monitored. This procedure was continued while the temperature of the reaction vessel was increased from ambient temperatures at the beginning up to 150° C. depending on the consumption rate of the fluorine gas. Addition of fluorine was stopped when the consumption rate of fluorine had dropped to a few mbar per hour. The preparation of the silver fluoride catalyst took several days until approximately 95 mol-% of the fluorine was consumed. Excess fluorine was removed by a fluorine resistant pumping system through a tube filled with soda-lime.

Example 2

Preparation of Perfluoro Tert-Butyl Hypofluorite $((CF_3)_3C\text{—}OF)$

Perfluoro tert-butanol (4.2 g, 17.8 mmol) was condensed in a stainless steel vessel equipped with carefully dried CsF (200 g) and allowed to reach room temperature. The mixture was well shaken before the vessel was connected to a steel line. At −78° C. elemental fluorine was added in small portions until the pressure reached 300 mbar and no fluorine was further consumed. After another 20 min at −78° C. excess fluorine was removed while the vessel was held at −196° C.

Example 3

Preparation of $(CF_3)_3C\text{—}O\text{—}O\text{—}C(CF_3)_3$ with Silver Fluoride The reaction mixture from example 2 was distilled into the second steel vessel containing the freshly prepared silver fluoride catalyst (22 g) according to example 1. After 5 days at −45° C. perfluoro bis(tert-butyl) peroxide was distilled out of the reaction vessel and trapped in a cooling trap held at −78° C. (2.6 g, 5.5 mmol, 62%).

Example 4

Preparation of perfluoro tert-butyl hypochlorite $((CF_3)_3C\text{—}OCl)$

Perfluoro tert-butanol (2.36 g, 10 mmol) was condensed in a stainless steel vessel equipped with carefully dried CsF (200 g) and allowed to reach room temperature. The mixture was well shaken before the vessel was connected to a stainless steel line. The vessel was cooled with liquid nitrogen and gaseous ClF (13 mmol) was added. The reaction mixture was slowly warmed to 0° C. After 12 hours, while the mixture was frequently shaken, the mixture was cooled to −78° C. and the excess of ClF was removed by a fluorine resistant pumping system through a tube filled with soda-lime. Yield.: 9.2 mmol, 92% hypochlorite

Example 5

Preparation of $(CF_3)_3C\text{—}O\text{—}O\text{—}C(CF_3)_3$ Under UV Irradiation The hypochlorite (1 mmol) of example 4 was distilled into a quartz flask (1 L) and irradiated using a Xenon high pressure lamp at 78° C. for 30 min. Trap-to-trap distillation of the reaction mixture yielded perfluoro bis(tert-butyl) peroxide (0.3 mmol, 57%) in a −78° C. trap and the volatile by-products $Cl_2$, $(CF_3)_2CO$ and $CF_3Cl$ were collected in a trap cooled at −196° C.

The invention claimed is:

1. A process for the manufacture of a compound of formula $R^1R^2R^3C\text{—}O\text{—}O\text{—}CR^4R^5R^6$ wherein $R^1$ to $R^6$ are chosen independently from F or a perfluorinated or partially fluorinated linear or branched alkyl group, the process comprising a step of reacting a hypofluorite mixture of $R^1R^2R^3COF$ and $R^4R^5R^6COF$ wherein $R^1R^2R^3COF$ and $R^4R^5R^6COF$ are the same or different, and/or a hypochlorite mixture of $R^1R^2R^3CoCl$ and $R^4R^5R^6CoCl$, wherein $R^1R^2R^3COCl$ and $R^4R^5R^6COCl$ are the same or different, with an inorganic fluoride in the absence of $COF_2$ and carbonyl fluorides of formula R'R''R'''CC(O)F, wherein R', R'' and R''' are selected independently from F or a perfluorinated or partially fluorinated linear or branched alkyl group, wherein the inorganic fluoride is selected from the group consisting of AgF, $AgF_2$, CuF, $CuF_2$, $BaF_2$, CsF, and $NiF_2$ or is a mixture of AgF and $AgF_2$.

2. The process of claim 1 wherein $R^2$ to $R^6$ are independently selected from the group consisting of F, $CF_3$, $C_2F_5$ and $C_3F_8$.

3. The process of claim 1 wherein the molar ratio of the inorganic fluoride to the hypofluorite mixture and/or the hypochlorite mixture is higher than 0.9.

4. The process of claim 1 comprising a step of reacting the hypofluorite mixture with AgF, $AgF_2$, or the mixture of AgF and $AgF_2$.

5. The process of claim 4 wherein AgF, $AgF_2$, or the mixture of AgF and $AgF_2$ is used in a molar ratio of higher than 1.0 compared to the hypofluorite mixture.

6. The process of claim 1, further comprising a step wherein the hypochlorite mixture is prepared in a reaction of an alcohol $R^1R^2R^3COH$ and $R^4R^5R^6COH$ or ketones $R^1R^2C(O)$ and/or $R^3R^4C(O)$, wherein $R^1$ to $R^6$ are chosen independently from the group consisting of F and a perfluorinated or partially fluorinated linear or branched alkyl group, with an inorganic fluoride selected from the group consisting of AgF, $AgF_2$, CuF, $CuF_2$, $BaF_2$, CsF, and $NiF_2$, and subsequently in a reaction in the presence of ClF.

7. The process of claim 1 wherein the process comprises the step of reacting a hypofluorite mixture of $R^1R^2R^3COF$ and $R^4R^5R^6COF$, and wherein the inorganic fluoride is selected from the group consisting of AgF, $AgF_2$, or a mixture of AgF and $AgF_2$.

8. The process of claim 2, wherein the compound of formula $R^1R^2R^3C\text{—}O\text{—}O\text{—}CR^4R^5R^6$ is chosen from the group consisting of $(CF_3)_3C\text{—}O\text{—}O\text{—}CF_3$, $(C_2F_5)(CF_3)_2C\text{—}O\text{—}O\text{—}CF_3$, $(C_2F_5)_2(CF_3)C\text{—}O\text{—}O\text{—}CF_3$, $(C_2F_5)_3C\text{—}O\text{—}O\text{—}CF_3$, $(CF_3)_3C\text{—}O\text{—}O\text{—}C(CF_3)_3$, $(C_2F_5)(CF_3)_2C\text{—}O\text{—}O\text{—}C(CF_3)_3$, $(C_2F_5)(CF_3)C\text{—}O\text{—}O\text{—}C(CF_3)_3$, $(C_2F_5)_3C\text{—}O\text{—}O\text{—}C(CF_3)_3$, $(C_2F_5)(CF_3)_2C\text{—}O\text{—}$ O—C($C_2F_5$)($CF_3$)$_2$, ($C_2F_5$)$_2$($CF_3$)C—O—O—C($C_2F_5$) ($CF_3$)$_2$, ($C_2F_5$)$_3$C—O—O—C($C_2F_5$)($CF_3$)$_2$, ($C_2F_5$)$_2$($CF_3$) C—O—O—C($C_2F_5$)$_2$($CF_3$), ($C_2F_5$)$_3$C—O—O—C($C_2F_5$)$_2$ ($CF_3$), ($C_2F_5$)$_3$C—O—O—C($C_2F_5$)$_3$, (i-$C_3F_7$)($CF_3$)$_2$C—O—O—$CF_3$, (i-$C_3F_7$)$_2$($CF_3$)C—O—O—$CF_3$, (i-$C_3F_7$)$_3$C—O—O—$CF_3$, (i-$C_3F_7$)($CF_3$)$_2$C—O—O—C($CF_3$)$_3$, (i-$C_3F_7$)$_2$ ($CF_3$)C—O—O—C($CF_3$)$_3$, (i-$C_3F_7$)$_3$C—O—O—C($CF_3$)$_3$, (i-$C_3F_7$)($CF_3$)$_2$C—O—O—C(i-$C_3F_7$)($CF_3$)$_2$, (i–$C_3F_7$)$_2$($CF_3$)C—O—O—C(i-$C_3F_7$)($CF_3$)$_2$, (i-$C_3F_7$)$_3$C—O—O—C(i-$C_3F_7$)($CF_3$)$_2$, (i-$C_3F_7$)$_2$($CF_3$)C—O—O—C(i-$C_3F_7$)$_2$($CF_3$), (i-$C_3F_7$)$_3$C—O—O—C(i-$C_3F_7$)$_2$($CF_3$), (i-$C_3F_7$)$_3$C—O—O—C(i-$C_3F_7$)$_3$, (i-$C_3F_7$)($CF_3$)($C_2F_5$)C—O—O—C($CF_3$)$_3$, (i-$C_3F_7$)($CF_3$)($C_2F_5$)C—O—O—C(i-$C_3F_7$)($CF_3$)$_2$, (i-$C_3F_7$) ($CF_3$)($C_2F_5$)C—O—O—C(i-$C_3F_7$)($C_2F_5$)($CF_3$), (i-$C_3F_7$) ($CF_3$)($C_2F_5$)C—O—O—C(i-$C_3F_7$)$_2$($CF_3$), (i-$C_3F_7$)($CF_3$) ($C_2F_5$)C—O—O—C(i-$C_3F_7$)$_3$ and CF($CF_3$)$_2$—O—O—CF ($CF_3$)$_2$, $CF_3CF_2$—O—O—$CF_3CF_2$, $CF_3$—O—O—$CF_3CF_2$, $CF_3$—O—O—$CF_3$.

9. The process of claim 1, wherein the inorganic fluoride is a mixture of AgF and $AgF_2$.

10. The process of claim 9, wherein the mixture of AgF and $AgF_2$ is obtained by treating silver wool with elemental fluorine.

11. The process of claim 10, wherein gaseous fluorine is added to the silver wool in small portions up, optionally while the pressure is monitored to a value of about 2 bar.

12. The process of claim 9, wherein the process comprises a first step consisting in preparing the mixture of AgF/$AgF_2$ by treating silver wool with elemental fluorine, and then a second step consisting in reacting the mixture of $R^1R^2R^3$COF and $R^4R^5R^6$COF and/or the mixture of $R^1R^2R^3$COCl and $R^4R^5R^6$COCl with said mixture of AgF/$AgF_2$ in the absence of $COF_2$ and carbonyl fluorides of formula R'R"R'"CC(O)F, wherein R', R" and R'" are selected independently from F or a perfluorinated or partially fluorinated linear or branched alkyl group.

* * * * *